United States Patent
Wunderer et al.

(10) Patent No.: US 6,763,721 B2
(45) Date of Patent: Jul. 20, 2004

(54) VERIFICATION OF THICKNESS MODULATIONS IN OR ON SHEET-TYPE PRODUCTS

(75) Inventors: Bernd Wunderer, München (DE); Ulrich Schanda, Holzkirchen (DE)

(73) Assignee: Giesecke & Devrient GmbH, Munich (DE)

(*) Notice: Subject to any disclaimer, the term of this patent is extended or adjusted under 35 U.S.C. 154(b) by 0 days.

(21) Appl. No.: 10/333,901

(22) PCT Filed: Jul. 30, 2001

(86) PCT No.: PCT/EP01/08821
§ 371 (c)(1),
(2), (4) Date: Apr. 25, 2003

(87) PCT Pub. No.: WO02/10716
PCT Pub. Date: Feb. 7, 2002

(65) Prior Publication Data
US 2003/0183012 A1 Oct. 2, 2003

(30) Foreign Application Priority Data
Jul. 31, 2000 (DE) .......... 100 37 664

(51) Int. Cl.⁷ .................................. G07D 7/08
(52) U.S. Cl. ............... 73/602; 73/159; 382/137
(58) Field of Search ............ 73/599, 602, 624, 73/159; 209/534; 382/137, 135; 702/171

(56) References Cited

U.S. PATENT DOCUMENTS

| 4,446,735 A | 5/1984 | Weilacher |
| 4,977,601 A | 12/1990 | Bicz |
| 5,691,474 A * | 11/1997 | Gerz .......................... 73/159 |
| 5,757,876 A | 5/1998 | Dam et al. |
| 5,986,457 A | 11/1999 | Kayani |
| 6,407,964 B1 | 6/2002 | Hornung et al. |
| 6,595,060 B2 * | 7/2003 | Wunderer et al. .......... 73/159 |

FOREIGN PATENT DOCUMENTS

| DE | 3048710 C2 | 7/1982 |
| DE | 3538711 A1 | 5/1987 |
| DE | 3610397 A1 | 10/1987 |
| DE | 4103832 A1 | 8/1992 |
| DE | 3888253 T2 | 3/1994 |
| DE | 19844447 A1 | 3/2000 |
| EP | 0300782 B1 | 1/1989 |
| EP | 0318229 A2 | 5/1989 |
| GB | 1181047 | 2/1970 |

* cited by examiner

Primary Examiner—John E. Chapman
(74) Attorney, Agent, or Firm—Bacon & Thomas, PLLC

(57) ABSTRACT

The invention relates to a method for verifying thickness modulations, in particular watermarks, in or on sheet material. To diminish the influence of disturbances from the surroundings and reduce the adjustment effort during production and maintenance of corresponding measuring systems, the sheet material is subjected to sound, in particular ultrasound, the sound transmitted through the sheet material and/or reflected on the sheet material is measured at a plurality of places on the sheet material, at least one value characteristic of the transmitted and/or reflected sound is generated for each of the places, and the thickness modulations are verified by comparing the values with predetermined reference values.

11 Claims, 2 Drawing Sheets

VERIFICATION OF THICKNESS MODULATIONS IN OR ON SHEET-TYPE PRODUCTS

BACKGROUND

This invention relates to a method for verifying thickness modulations, in particular watermarks, in or on sheet material, in particular documents of value or security documents.

In machine authenticity testing of documents of value or security documents such as bank notes, the verification of watermarks as an authenticity feature plays an important part. This is frequently done using optical methods by which a bank note to be checked is irradiated with light and the light transmitted through the bank note is detected with the aid of a one- or two-dimensional photodiode array. The obtained data are compared with data of a reference watermark, the bank note being classified as authentic or false in accordance with the degree of match.

However, optical methods are generally disadvantageous in that measurements can be easily disturbed by ambient light, and the sensitivity of the photodetectors customarily used as well as the strength of the light sources used are subject to temporal fluctuations that likewise falsify measurement. In addition, an imaging optic comprising lenses and/or diaphragms is generally required, which necessitates high adjustment effort during production and maintenance of corresponding measuring systems.

SUMMARY

The invention is based on the problem of providing an improved method for verifying thickness modulations in or on sheet material that in particular reduces the influence of disturbances and the adjustment effort during production and maintenance of corresponding measuring systems.

This problem is solved by the invention in that the sheet material is subjected to sound, in particular ultrasound, the sound transmitted through the sheet material and/or reflected on the sheet material is measured at a plurality of places on the sheet material, and at least one value characteristic of the transmitted and/or reflected sound is generated for each of the places. Verification of thickness modulations is then done by comparing the generated characteristic values with predetermined reference values. The use of sound, in particular ultrasound, avoids the influence of disturbances, for example due to ambient light, and in addition reduces the adjustment effort.

In a preferred embodiment of the method it is provided that the places where the transmitted or reflected sound is measured are located on at least one track extending linearly on the sheet material. The distances between the individual places can be selected so as to obtain a certain spatial resolution of the watermark to be measured. In particular, the individual places can also touch or overlap each other so that a continuous track is measured on the sheet material.

The invention will now be explained in more detail with reference to figures, in which:

DETAILED DESCRIPTION

Figure 1:
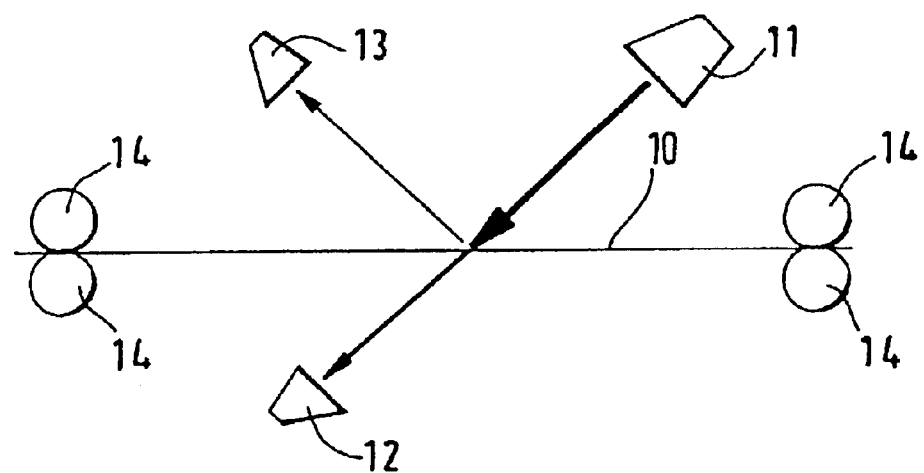
FIG. 1 shows an apparatus for carrying out the inventive method.

FIG. 1 shows an apparatus for carrying out the inventive method. Sheet material 10 under examination, in this case a bank note, is transported between ultrasonic transmitter 11 and ultrasonic detector 12 with the aid of a transport device shown here only sketchily by transport rolls 14. Sound emitted by ultrasonic transmitter 11 and partially transmitted through sheet material 10 is detected by ultrasonic detector 12. Additionally or alternatively, partially reflected ultrasound can be detected by further ultrasonic detector 13, as shown in the figure. To avoid spurious signals from possible reflection of sound fractions between ultrasonic transmitter 11 and ultrasonic detector 12 or 13, ultrasonic transmitter 11, sheet material 10 and ultrasonic detector 12, 13 are disposed obliquely to each other so as to screen out such reflections from the beam path between ultrasonic transmitter 11 and ultrasonic detector 12, 13. As shown in the example, sheet material 10 is thus subjected to ultrasound at a nonright angle. Spurious signals can moreover be eliminated by determining the sound propagation time between ultrasonic transmitter 11 and ultrasonic detector 12, 13 and, for actual measurement, switching on ultrasonic detector 12, 13 delayed by the sound propagation time and switching it off after twice the sound propagation time of the latest.

Figure 2:
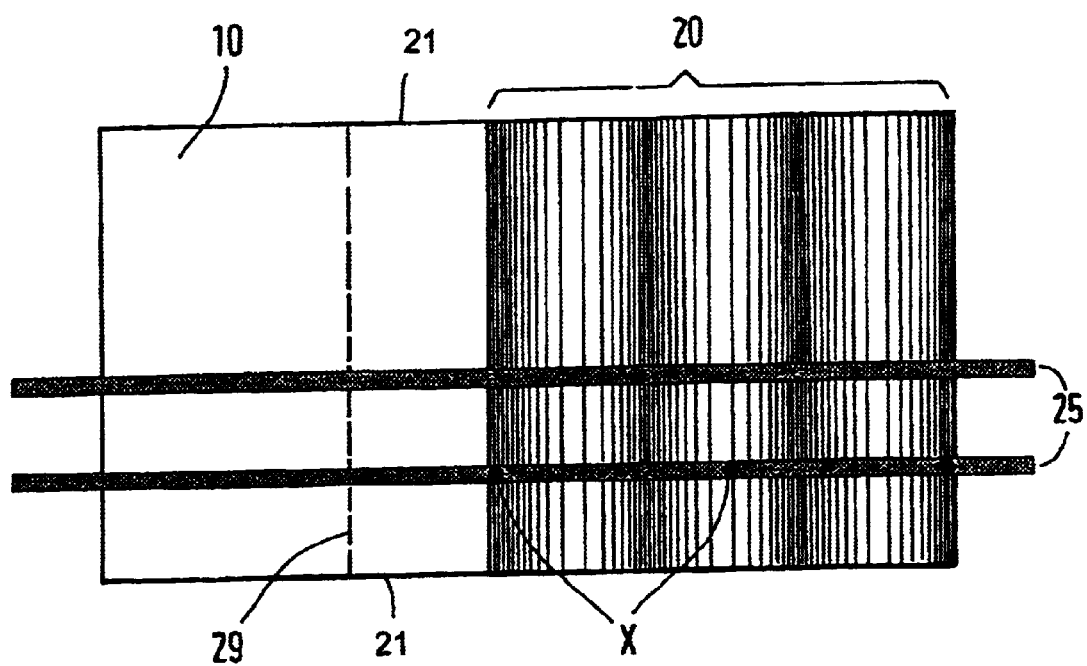
FIG. 2 shows a bank note having a periodic watermark with additionally marked tracks.

FIG. 2 shows bank note 10 with watermark 20 having thicker and thinner areas alternating periodically in the direction of longitudinal edges 21. However, the inventive method is suitable in general for verifying watermarks with any pattern, for example a periodic pattern obliquely to longitudinal edges 21 of the bank note or any nonperiodic pattern. In addition to watermark 20, bank note 10 shown here has security thread 29. FIG. 2 in addition indicates two tracks 25 along which bank note 10 is measured at places X. The figure shows by way of example three places X located in the area of watermark 20. Such track measurement is realized for example with the aid of the apparatus shown in FIG. 1. Sheet material is transported, preferably at constant speed, past ultrasonic detectors 12, 13. Reflected and/or transmitted sound is then measured at certain instances of time so that measurement is done at different place X at every time of measurement. Track measurement can also be realized by measuring reflected and/or transmitted sound with a plurality of detectors disposed in a row (not shown), each detector being assigned one place on sheet material 10.

Figure 3:
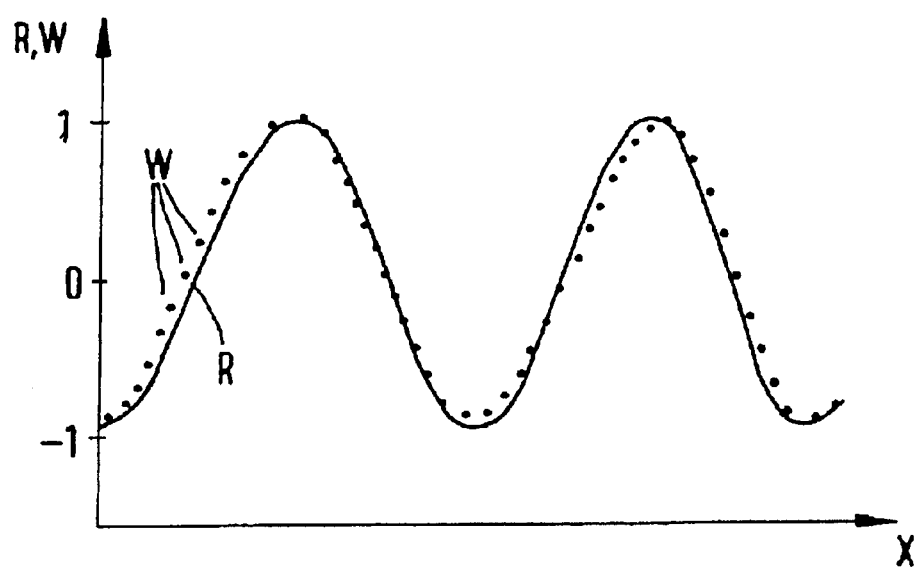
FIG. 3 shows a graph of values and corresponding reference values.

FIG. 3 shows a diagram with values W determined in the area of watermark 20 on track 25 extending linearly on bank note 10. Values W are plotted here over associated places X where they were measured. The shown case involves a track measurement whereby individual places X are a certain distance apart. In this example the determined values show a substantially sinusoidal pattern with a certain spatial frequency, i.e. periods per unit length. Additionally, this diagram shows reference values R (continuous curve) that represent a kind of nominal pattern of the watermark to be verified, with a sinusoidal pattern and certain spatial frequency. There is generally a phase difference between the pattern of values W and the pattern of reference value R, which is caused for example by a watermark extending obliquely to track 25. Values W and reference values R shown in the diagram were therefore shifted relative to each other so as to reduce, in this case minimize, the phase difference. As likewise indicated by the shown diagram, values W and reference values R were standardized.

Verification of the thickness modulations in sheet material 10 due to watermark 20 can now be done by comparing values W with reference values R. Comparison of values W with reference values R can be done using a correlation function determined by multiplying individual values W by reference values R at places X. If the bulk of the values of the correlation function calculated at individual places X are in the range between about 0.9 and 1.0, for example, there is a very good correlation, i.e. the measured thickness modulation of watermark 20 matches the predetermined pattern of reference values R very well so that the watermark to be verified is to be classified as authentic.

A correlation factor can in addition be determined from the individual values of the correlation function by averaging to be used in addition or as an alternative to the correlation function for comparing the value pattern with the reference value pattern. The correlation factor can then be compared with a predetermined threshold value. If the correlation factor is above this threshold value, for example above 0.9, there is a very good correlation and measured watermark 20 can be considered authentic. Calculation of the correlation function or correlation factor is a method for comparing values W with reference values R that is especially easy to handle in terms of computing.

To increase the reliability of the method it can also be provided that those values W located in the area of disturbances, in particular due to soiling, foreign bodies or wear, of the thickness modulations to be verified are not used for comparison with the predetermined reference values. For example, the values of the corresponding places where the disturbances are located are set at zero and the number of thus generated zeros is recorded. These values do not make any contribution during calculation of the correlation factor so that their number must be subtracted from the number of values W over which averaging is to be done. This permits the influence of disturbances to be eliminated in an especially simple way.

Analogously to the verification of periodic watermarks as explained above, nonperiodic watermarks are examined by comparing values W determined on linear track 25 with reference values R having a nonperiodic pattern. The predetermined nonperiodic pattern of reference values R can for example comprise information about the bank note or kind of bank note, e.g. value, country of origin or issue year. This information is preferably contained in the nonperiodic pattern in encoded form. The inventive method is therefore suitable in particular for examining or verifying encoded watermarks on or in bank notes.

What is claimed is:

1. A method for verifying thickness modulations in or on sheet material wherein the sheet material is subjected to sound, sound transmitted through the sheet material and/or reflected from the sheet material is measured at a plurality of places on the sheet material, at least one value characteristic of the transmitted and/or reflected sound is generated for each of the places, and verification of thickness modulations is done by comparing the values with predetermined reference values, comprising the steps:

comparing the values with the reference values using a correlation factor that is determined by multiplying the individual values by the reference values and averaging the thus obtained results, wherein those values located in the area of disturbances of the thickness modulations to be verified are not used for comparison with the reference values.

2. The method according to claim 1, wherein the places where the transmitted or reflected sound are measured are located on at least one track extending linearly on the sheet material.

3. The method according to claim 1, wherein reference values with a periodic pattern are predetermined.

4. The method according to claim 3, wherein reference values with a sinusoidal pattern are predetermined.

5. The method according to claim 3, wherein a certain spatial frequency is predetermined for the periodic pattern of the reference values.

6. The method according to claim 3, wherein the values and the reference values are shifted relative to each other before comparison so as to reduce a phase difference possibly present between the values and the reference values.

7. The method according to claim 1, wherein reference values with a nonperiodic pattern are predetermined.

8. The method according to claim 7, wherein the nonperiodic pattern of the reference values contain a coding.

9. The method according to claim 1, wherein the values and/or the reference values are standardized before multiplying the individual values by the reference values.

10. The method according to claim 1, wherein the correlation factor is compare with at least one predetermined threshold value.

11. The method according to claim 1, wherein the disturbances of the thickness modulations are creases, soiling, foreign bodies and areas of wear of the sheet material.

* * * * *